(12) United States Patent
Bramlett et al.

(10) Patent No.: US 10,839,948 B2
(45) Date of Patent: Nov. 17, 2020

(54) MICROFLUIDIC INFORMATION-ENCODING POLYMER DATA STORAGE

(71) Applicant: Intel Corporation, Santa Clara, CA (US)

(72) Inventors: Brian W. Bramlett, Portland, OR (US); Amar S. Basu, Troy, MI (US)

(73) Assignee: Intel Corporation, Santa Clara, CA (US)

( * ) Notice: Subject to any disclaimer, the term of this patent is extended or adjusted under 35 U.S.C. 154(b) by 902 days.

(21) Appl. No.: 15/394,484

(22) Filed: Dec. 29, 2016

(65) Prior Publication Data
US 2018/0189448 A1    Jul. 5, 2018

(51) Int. Cl.
| | |
|---|---|
| *G01N 33/48* | (2006.01) |
| *G01N 33/50* | (2006.01) |
| *G16H 10/60* | (2018.01) |
| *G06N 3/12* | (2006.01) |
| *B01L 3/00* | (2006.01) |

(52) U.S. Cl.
CPC .............. *G16H 10/60* (2018.01); *G06N 3/123* (2013.01); *B01L 3/502792* (2013.01)

(58) Field of Classification Search
None
See application file for complete search history.

(56) References Cited

U.S. PATENT DOCUMENTS

| | | |
|---|---|---|
| 8,137,917 B2 | 3/2012 | Pollack et al. |
| 2005/0053968 A1 | 3/2005 | Bharadwaj et al. |
| 2010/0124759 A1 | 5/2010 | Wang et al. |
| 2011/0190146 A1 | 8/2011 | Boehm et al. |
| 2015/0261664 A1 | 9/2015 | Goldman et al. |
| 2015/0269313 A1 | 9/2015 | Church |
| 2016/0122802 A1 | 5/2016 | Frayling |

FOREIGN PATENT DOCUMENTS

| | | | |
|---|---|---|---|
| WO | WO-2014199113 A1 | * | 12/2014 |
| WO | WO2016-164779 A1 | | 10/2016 |

OTHER PUBLICATIONS

Griffith et al. Corrdinating multiple droplets in planar array digital microfluidic systems. The International Journal of Robotics Research, vol. 24, pp. 933-949. (Year: 2005).*

(Continued)

*Primary Examiner* — Russell S Negin
(74) *Attorney, Agent, or Firm* — Schwabe, Williamson & Wyatt, P.C.

(57) ABSTRACT

Embodiments herein relate to data storage and retrieval using information-encoding polymers encapsulated in droplets stored in a microfluidic droplet storage array. In various embodiments, a data storage apparatus may include a microfluidic droplet storage array to store one or more droplets containing one or more information-encoding polymer molecules in one or more droplet storage locations, and an interface coupled with the microfluidic droplet storage array to receive the one or more droplets from a data writer that writes the one or more droplets into the microfluidic droplet storage array. Other embodiments may be described and/or claimed.

15 Claims, 5 Drawing Sheets

(56) References Cited

OTHER PUBLICATIONS

International Search Report and Written Opinion dated Feb. 28, 2018 for International Patent Application No. PCT/US2017/061400, 13 pages.
Jin, Si Hyung et al., "A programmable microfluidic static droplet array for droplet generation, transportation, fusion, storage, and retrieval", Lab on a Chip, 2015, vol. 15, No. 18, pp. 3677-3686.
Bornholt, James et al., "A DNA-Based Archival Storage System", Association for Computing Machinery, Apr. 2016, vol. 51, No. 2, pp. 637-649.
Leung, K., et. al. "A Droplet-Based Microfluidic Random Access Memory for Genetic Analysis of Single Cells," 15th International Conference on Miniaturized Systems for Chemistry and Life Sciences Oct. 2-6, 2011, Seattle, Washington, USA, pp. 729-731.

\* cited by examiner

MICROFLUIDIC INFORMATION-ENCODING POLYMER DATA STORAGE

FIELD

Embodiments of the present disclosure generally relate to the field of data storage and, more particularly, to data storage and retrieval using information-encoding polymers.

BACKGROUND

Growth in data creation and demand for storage of some portion of the new data are both increasing exponentially. By some estimates, this growth exceeds the industrial capacity to build enough storage system capacity using legacy technologies to meet forecasted demand. Some experiments have been performed to explore the use of information-encoding polymers such as deoxyribonucleic acid (DNA) as a data storage medium. However, these experiments have typically stored relatively small amounts of information in DNA dissolved in bulk, with corresponding difficulty in data storage and retrieval such that the techniques are not amenable to scaling up for storage of large amounts of data.

BRIEF DESCRIPTION OF THE DRAWINGS

Embodiments of the data storage and retrieval devices and methods of the present disclosure may overcome these limitations. The techniques will be readily understood by the following detailed description in conjunction with the accompanying drawings. To facilitate this description, like reference numerals designate like structural elements. Embodiments are illustrated by way of example, and not by way of limitation, in the figures of the accompanying drawings.

DETAILED DESCRIPTION

Embodiments of the present disclosure describe devices, systems, and techniques to store and retrieve data in a microfluidic droplet storage array using information-encoding polymers encapsulated in droplets. In various embodiments, a data storage apparatus may include a microfluidic droplet storage array to store one or more droplets containing one or more information-encoding polymer molecules in one or more droplet storage locations, and an interface coupled with the microfluidic droplet storage array to receive the one or more droplets from a data writer that writes the one or more droplets into the microfluidic droplet storage array.

In the following description, various aspects of the illustrative implementations will be described using terms commonly employed by those skilled in the art to convey the substance of their work to others skilled in the art. However, it will be apparent to those skilled in the art that embodiments of the present disclosure may be practiced with only some of the described aspects. For purposes of explanation, specific numbers, materials, and configurations are set forth in order to provide a thorough understanding of the illustrative implementations. It will be apparent to one skilled in the art that embodiments of the present disclosure may be practiced without the specific details. In other instances, well-known features are omitted or simplified in order not to obscure the illustrative implementations.

In the following detailed description, reference is made to the accompanying drawings that form a part hereof, wherein like numerals designate like parts throughout, and in which is shown by way of illustration embodiments in which the subject matter of the present disclosure may be practiced. It is to be understood that other embodiments may be utilized and structural or logical changes may be made without departing from the scope of the present disclosure. Therefore, the following detailed description is not to be taken in a limiting sense, and the scope of embodiments is defined by the appended claims and their equivalents.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B, and C).

The description may use perspective-based descriptions such as top/bottom, in/out, over/under, and the like. Such descriptions are merely used to facilitate the discussion and are not intended to restrict the application of embodiments described herein to any particular orientation.

The description may use the phrases "in an embodiment," or "in embodiments," which may each refer to one or more of the same or different embodiments. Furthermore, the terms "comprising," "including," "having," and the like, as used with respect to embodiments of the present disclosure, are synonymous.

The term "coupled with," along with its derivatives, may be used herein. "Coupled" may mean one or more of the following. "Coupled" may mean that two or more elements are in direct physical or electrical contact. However, "coupled" may also mean that two or more elements indirectly contact each other, but yet still cooperate or interact with each other, and may mean that one or more other elements are coupled or connected between the elements that are said to be coupled with each other. The term "directly coupled" may mean that two or more elements are in direct contact.

As used herein, the term "module" may refer to, be part of, or include an Application Specific Integrated Circuit (ASIC), an electronic circuit, a processor (shared, dedicated, or group), and/or memory (shared, dedicated, or group) that execute one or more software or firmware programs, a combinational logic circuit, and/or other suitable components that provide the described functionality. In some embodiments, the term "module" may refer to a fluidic handling module, a module for synthesizing information encoding polymer molecules such as DNA oligomers, or a module for sequencing information encoding polymer molecules such as DNA oligomers.

Figure 1:
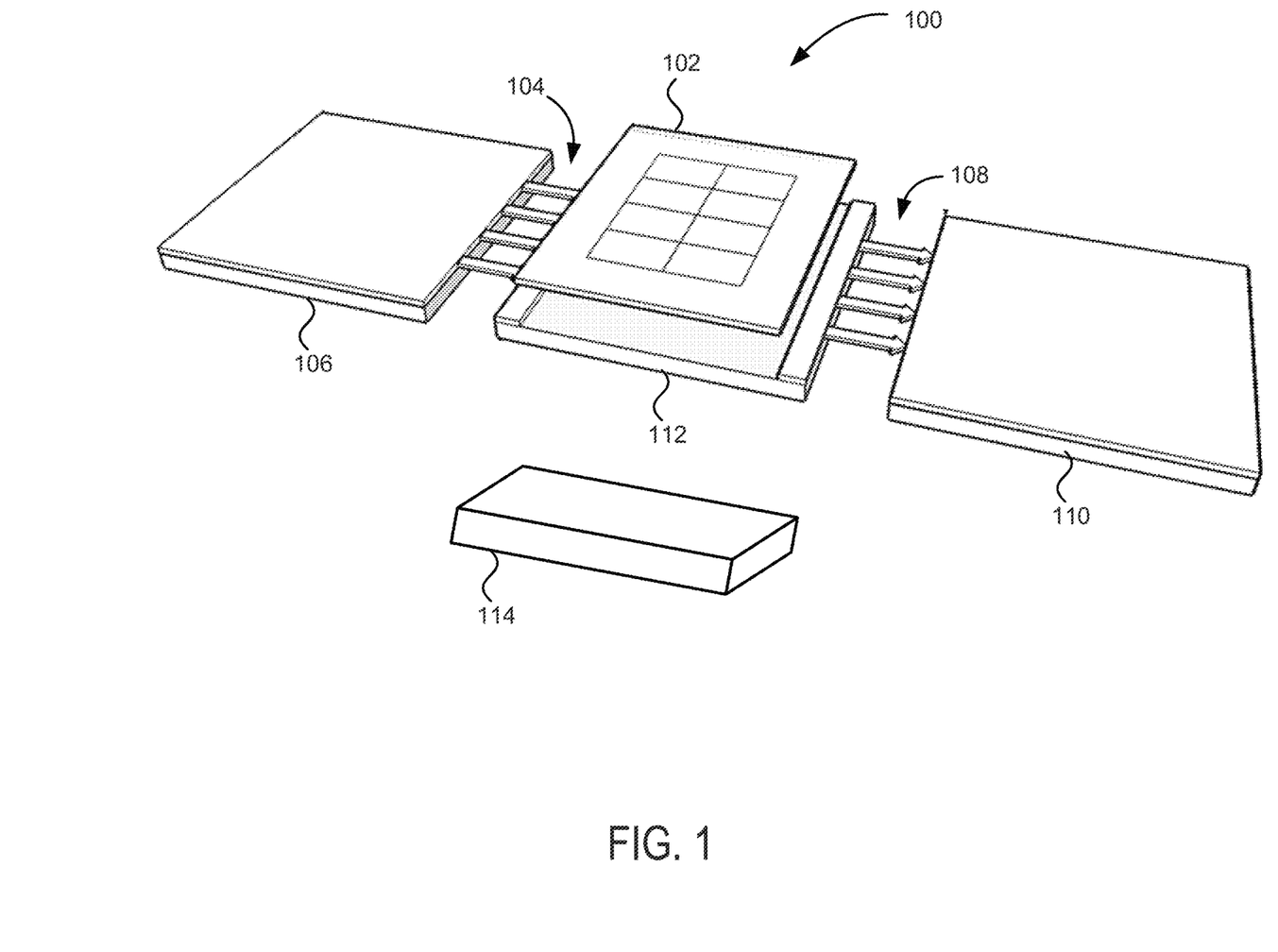
FIG. 1 is a block diagram of a data storage apparatus, according to various embodiments.

FIG. 1 is a block diagram of a data storage apparatus 100, according to various embodiments. In some embodiments, the data storage apparatus 100 may include a microfluidic droplet storage array 102 to store one or more droplets containing one or more information-encoding polymer molecules in one or more droplet storage locations. In various embodiments, the microfluidic droplet storage array 102 may be a spatially addressable array where droplets are stored on a two dimensional grid. In some embodiments, information encoding polymer molecules such as DNA may be attached to a particle or a bead. In some embodiments, the particles or beads may themselves be in a droplet that may be stored. In other embodiments, the particles or beads may be in solution without being contained in a droplet. In various embodiments, the microfluidic droplet storage array 102 may have a planar architecture, where fluidic droplet transport channels for droplet motion (not shown for clarity) and storage locations may be in the same plane. In some embodiments, the planar architecture may be stacked to increase storage density. In various embodiments, the microfluidic droplet storage array 102 may include stacked transport layers (e.g., similar to metal layers in complementary metal oxide semiconductor (CMOS) technology) which may be used to route droplets or beads to their respective locations. In some embodiments, droplets or beads may travel vertically between layers. In some embodiments, the storage locations may be storage wells.

In various embodiments, the data storage apparatus 100 may include a first interface 104 coupled with the microfluidic droplet storage array 102 to receive the one or more droplets from a data writer 106 that writes one or more droplets into the microfluidic droplet storage array 102. In some embodiments, the data writer 106 may include a synthesis module that may synthesize one or more information-encoding polymer molecules, such as a DNA sequence, based at least in part on input data. In various embodiments, the data writer 106 may synthesize the information-encoding polymer molecules based at least in part on the input data and an error correction coding scheme so the input data can be later recovered from the information-encoding polymer molecules even if some errors are introduced during a writing, storage, and/or reading process. In some embodiments, the data writer 106 may synthesize redundant copies of the information-encoding polymer molecules to make up for loss of molecules from droplets, detection of contamination, and/or to allow for greater throughput during reading. In some embodiments, the data writer 106 may synthesize approximately ten to one hundred redundant copies. Different redundancy levels may be used in other embodiments. In various embodiments, the data writer 106 may encapsulate the one or more information-encoding polymer molecules into a droplet which is then directed to the microfluidic droplet storage array 102. In some embodiments, the data writer 106 may attach the one or more information encoding polymer molecules to a particle or bead and/or may encapsulate the particle or bead into a droplet. In embodiments, the particle or bead may then be directed to the microfluidic droplet storage array 102. The information-encoding molecules encapsulated in the droplets may be bare DNA strands in some embodiments. In various embodiments, single or double stranded DNA may be anchored to a bead or particle. In some embodiments, the one or more information-encoding polymer molecules may be encapsulated in an ionic solution such as water. In various embodiments, the droplets may be surrounded by air, oil, or some other gas or liquid during transport and/or storage.

In some embodiments, the data storage apparatus 100 may include a second interface 108 coupled with the microfluidic droplet storage array 102 to allow one or more of the one or more information-encoding polymer molecules to move from one or more of the droplet storage locations to a data reader 110. In various embodiments, the data reader 110 may include a nanopore sequencer, a pyrosequencer, an enzymatic sequencer, and/or a sequencer using any other suitable technology.

In various embodiments, the droplets may range from approximately 1 femtoliter in volume to approximately 1 picoliter (pL) in volume. In various embodiments, droplet volumes of up to 100 pL or more may be used in some implementations that may use electrowetting on dielectric (EWOD). The droplets may have higher or lower volumes in some embodiments. In various embodiments, the storage locations of the microfluidic droplet storage array 102 may have a center-to center spacing of approximately 20 microns, resulting in an area density of droplet storage locations of approximately 2,500 droplets/millimeter (mm)$^2$ or 250,000 droplets/centimeter (cm)$^2$. Different storage location spacing and/or arrangements such as a three dimensional (3D) grid may be used in other embodiments. In some embodiments, the droplets may contain less than approximately 2% information-encoding molecules (e.g., DNA) by volume. The droplets may contain a greater percentage of information-encoding molecules in other embodiments.

In various embodiments, where DNA may be used as an information-encoding molecule, molecules of at least approximately one hundred base pairs may be included in each droplet. In some embodiments, strands of a few hundred base pairs may be encapsulated in the droplets. In other embodiments, molecules of greater lengths may be used. In various embodiments, multiple different information-encoding molecules (e.g., strands of DNA) may be included in each droplet with redundant copies of each different information-encoding molecule in the droplet. In other embodiments, a single information-encoding molecule and its associated redundant copies may be encapsulated in the droplet. In various embodiments, encoded data using several megabases may be contained in a droplet using information-encoding molecules having hundreds or thousands of bases in each strand. In some embodiments, approximately six giga bases may be included in a picoliter scale volume, resulting in approximately 1.5 peta bases (3 raw petabits without encoding or error correction) being stored per square centimeter. Other lengths, volumes, and/or configurations may be used in other embodiments. In various embodiments, linear information-encoding molecules and/or circular information-encoding molecules may be encapsulated in the droplets. In some embodiments, where longer strands of at least approximately one hundred kilobase pairs may be encapsulated in the droplets, the data writer 106 may incorporate structural design elements into the information-encoding molecules encapsulated in the droplets to affect tertiary structure of the molecules and/or may incorporate additional types of molecules (e.g., proteins) to affect quaternary structure of the molecules in a manner similar to the function of histones in chromatin.

In various embodiments, a controller 112 may be coupled with the microfluidic droplet storage array 102. In embodiments, the controller 112 may be an electronic element to control storage and retrieval of droplets. In some embodiments, the controller 112 may be to generate controlled forces to cause the one or more droplets to move from the first interface 104 to one or more locations in the microfluidic droplet storage array 102. In various embodiments, the controller 112 may also be to generate controlled forces to cause one or more of the one or more droplets to move from one or more of the one or more locations in the microfluidic droplet storage array 102 to the second interface 108. In some embodiments, the controlled forces generated by the controller 112 may be electrowetting control signals. In various embodiments, the controlled forces generated by the controller 112 may include electrophoresis, dielectrophoresis, acoustic, hydrodynamic, pneumatic, magnetic and/or other types of forces or signals. In some embodiments, the microfluidic droplet storage array 102 may use a multiplexed pneumatic valve array where n droplets may be addressably stored with k*log base2(n) external pneumatic controllers, where k is an integer value. In various embodiments, the controller 112 may be implemented in hardware, firmware, a field programmable gate array (FPGA), an application specific integrated circuit (ASIC), with software and one or more processors, or some combination thereof.

In some embodiments, the microfluidic droplet storage array 102 and the controller 112 may each form part of an integrated storage module where the electronic control and microfluidic components are manufactured on a single substrate and process. In other embodiments, the microfluidic droplet storage array 102 and the controller 112 may each be part of a modular storage module where the electronic control and microfluidic components are manufactured separately and affixed together. In some embodiments, the controller 112 may include complementary metal oxide semiconductor (CMOS) integrated circuit technology and/or may be implemented on a silicon substrate. In various embodiments, the controller 112 may be implemented on high resolution packaging technology (e.g., printed circuit board (PCB) or packaging technology), thin film transistor arrays, polymer substrates, or with any other suitable technology or integrated combination of technologies.

In some embodiments, the data storage apparatus 100 may include an amplification module 114 that may be coupled with the second interface 108 and/or the first interface 104, connections not shown for clarity. In various embodiments, the amplification module 114 may be to receive a droplet or portion of a droplet containing a redundant copy of an information-encoding polymer molecule having another copy read by the data reader 110. In some embodiments, the amplification module 114 may be to generate one or more copies of the received redundant copy of the information-encoding polymer molecule, encapsulate the one or more copies in a droplet, and move the droplet to the first interface 104 to be stored in the microfluidic droplet storage array 102 such that when data is read by the data reader 110, the information may persist in the microfluidic droplet storage array 102 by amplifying a portion of the original information-encoding polymer molecules through copying with the amplification module 114, and storing the copies back into the microfluidic droplet storage array 102. In some embodiments, encapsulation of one or molecules in a droplet and storage of the droplets containing specific, small subsets of information in the microfluidic droplet storage array 102 may provide for quick access to the information and maintenance of the droplets in an addressable state for long periods of time (e.g., years to decades). In various embodiments, the data storage apparatus 100 may not include the amplification module 114 and/or data persistence may be achieved by resynthesizing one or more information-encoding molecules with the data writer 106 when droplets are read by the data reader 110 rather than diverting a portion of the information-encoding molecules to an amplification module for copying. In some embodiments, a reading of data by the data reader 110 may be a destructive read, without copying by an amplification module or resynthesizing by the data writer 106.

In some embodiments, the data storage apparatus 100 may be a storage and retrieval component of a memory device architecture, and/or may form the core of an approach to storing a known subset of molecules in an array of addressable containers. In some embodiments, one or more of the data writer 106, the microfluidic droplet storage array 102, the controller 112, the data reader 110, and/or the amplification module 114 may be separate devices, may be components integrated into an assembly, or may be fabricated as part of the same system using a common manufacturing process. In various embodiments, the data storage apparatus 100 may be a fully integrated or a separable media implementation of a large scale data storage system and may exceed many limits of legacy magnetic, optical, and electronic storage technologies such as density, capacity, persistence, and/or cost. In some embodiments, the data storage apparatus 100 may support scaling to very high capacities (e.g., petabyte or exabyte systems), while addressing random access, latency, and access time issues. In various embodiments, the data storage apparatus 100 may be used for an application such as storage of video data where data may be continuously stored, with data representing a short time frame being stored in each location of the microfluidic droplet storage array 102 as encoded by one or more information-encoding polymer molecules encapsulated in a droplet. In some embodiments, the data storage apparatus 100 may provide for random storage and access in addressable locations of the microfluidic droplet storage array 102. In other embodiments, the data storage apparatus may use a first-in first-out (FIFO) storage and retrieval process. In various embodiments, an index associated with the microfluidic droplet storage array 102 may be generated and maintained by the data storage apparatus 100.

Figure 2:
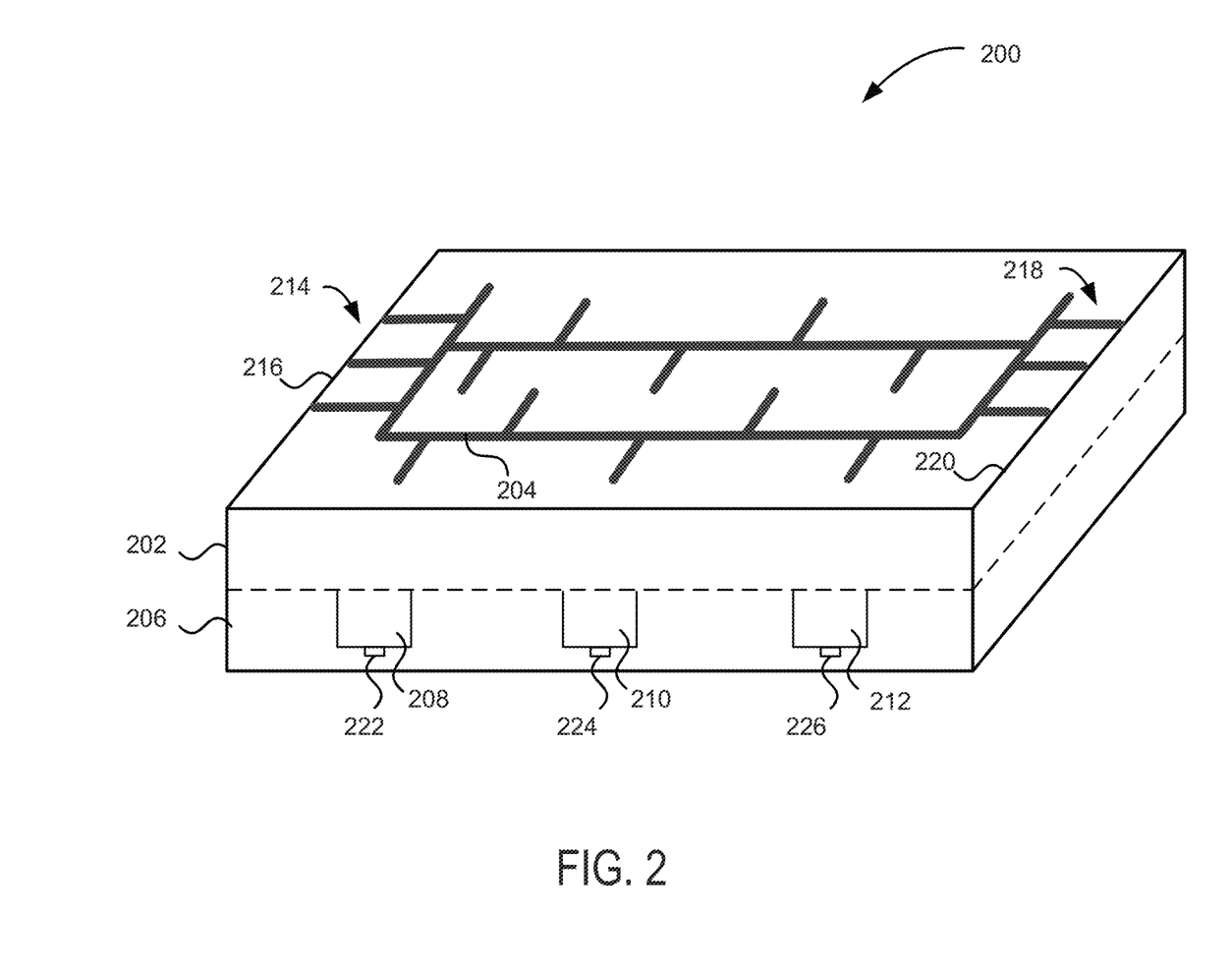
FIG. 2 is a block diagram of a microfluidic droplet storage array, according to various embodiments.

FIG. 2 is a block diagram of a microfluidic droplet storage array 200, according to various embodiments. In some embodiments, the microfluidic droplet storage array 200 may have a layered architecture with fluidic droplet transport channels in a first plane and droplet storage locations in a second plane. In various embodiments, a first layer 202 may include fluidic droplet transport channels 204 in the first plane and a second layer 206 may include droplet storage locations in the second plane, shown as a first droplet storage location 208, a second droplet storage location 210, and a third droplet storage location 212. It should be understood that the particular configuration of fluidic droplet transport channels 204 and droplet storage locations is shown for purposes of illustration only and any other suitable configuration of fluidic droplet transport channels and/or droplet storage locations may be used in various embodiments. In some embodiments, one or more of the storage locations 208, 210, 212 may be storage wells. In some embodiments, the microfluidic droplet storage array 200 may be included in the data storage apparatus 100 rather than the microfluidic droplet storage array 102 and may be coupled with the data writer 106, the data reader 110, and/or the controller 112 in similar fashion to that described with respect to the microfluidic droplet storage array 102. In various embodiments, use of a layered architecture may improve the density of storage. In some embodiments, the microfluidic droplet storage array 200 and/or the microfluidic droplet storage array 102 may be used as removable media in the data storage apparatus 100.

In some embodiments, a first subset 214 of the fluidic droplet transport channels 204 may form a first interface at a first edge 216 of the microfluidic droplet storage array 200. In various embodiments, a second subset 218 of the fluidic droplet transport channels 204 may form a second interface at a second edge 220 of the microfluidic droplet storage array 200. In some embodiments, one or more channels of the first subset 214 may be to receive droplets from the data writer 106 and/or one or more channels of the second subset 218 may be to transport droplets to the data reader 110 and/or the amplification module 114. In various embodiments, the microfluidic droplet storage array 200 may include a first addressable electrode 222, a second addressable electrode 224, and a third addressable electrode 226 to guide and eject droplets to and/or from the droplet storage locations 208, 210, and 212 respectively.

Figure 3:
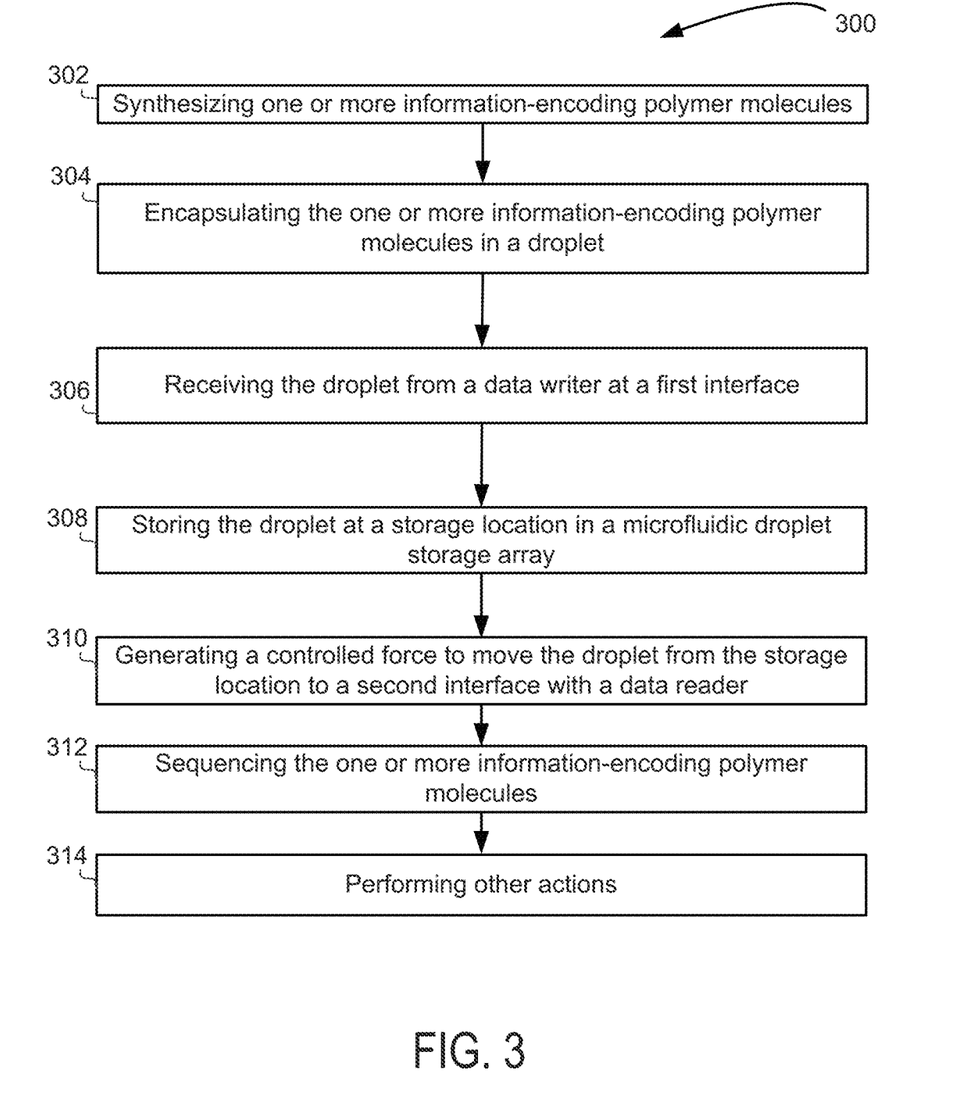
FIG. 3 is a flow diagram illustrating a method of storing and retrieving data, according to various embodiments.

FIG. 3 is a flow diagram illustrating a method 300 of storing and retrieving data, according to various embodiments. In embodiments, some or all of the method 300 may be practiced by components shown and/or described with respect to the data storage apparatus 100 and/or the microfluidic droplet storage array 200 of FIG. 1 and/or FIG. 2.

In some embodiments, the method 300 may include synthesizing one or more information-encoding polymer molecules at a block 302 (e.g., with data writer 106). In various embodiments, the method 300 may include encapsulating the one or more information-encoding polymer molecules in a droplet at a block 304. In some embodiments, the method 300 may include attaching the one or more information-encoding polymer molecules to a particle or bead (e.g., a latex or hydrogel bead) in addition to or instead of encapsulating the one or more information-encoding polymer molecules at the block 304. In some embodiments, at a block 306, the method 300 may include receiving the droplet containing the one or more information-encoding polymer molecules from a data writer at a first interface. In various embodiments, the method 300 may include storing the droplet at a storage location in a microfluidic droplet storage array (e.g., microfluidic droplet storage array 102 or 200) at a block 308. In some embodiments, the method 300 may include generating a controlled force to move the droplet from the storage location to a second interface with a data reader at a block 310 (e.g., with controller 112). In various embodiments, at a block 312, the method 300 may include sequencing the one or more information-encoding polymer molecules (e.g., with data reader 110). In some embodiments, the method 300 may include performing other actions at a block 314.

Figure 4:
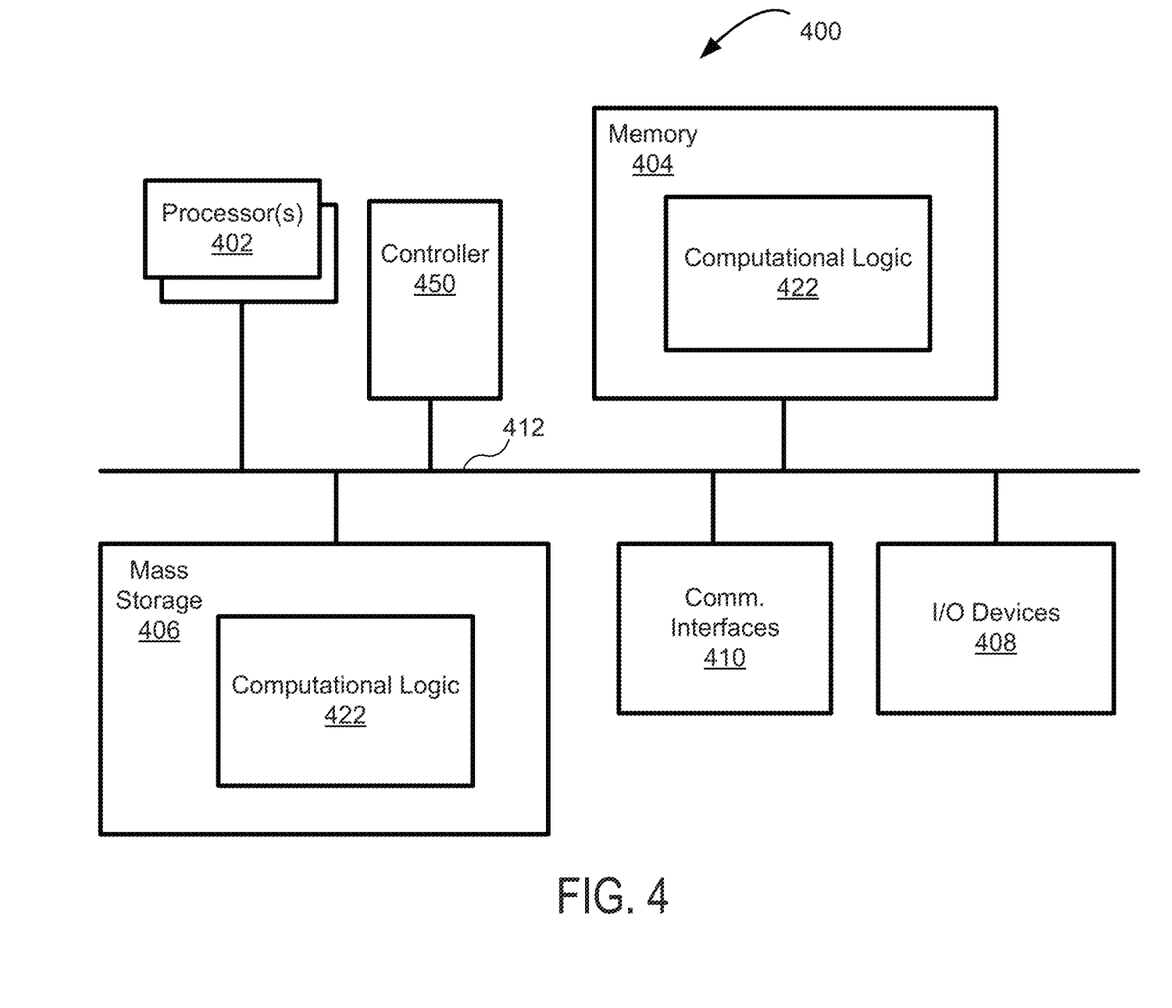
FIG. 4 schematically illustrates an example computer device to be used in data storage and retrieval, according to various embodiments.

FIG. 4 illustrates an example computer device 400 that may include components corresponding to and/or implementing various components and methods of FIGS. 1-3, such as data storage apparatus 100 with controller 112, described with respect to FIG. 1, in accordance with various embodiments. As shown, computer device 400 may include one or more processors 402, each having one or more processor cores, and system memory 404. The processor 402 may include any type of processors, and may include single or multi-core microprocessors, and the like. The processor 402 may be implemented as an integrated circuit. The computer device 400 may include mass storage devices 406 (such as diskette, hard drive, volatile memory (e.g., dynamic random-access memory (DRAM), compact disc read-only memory (CD-ROM), digital versatile disk (DVD), and so forth). In general, system memory 404 and/or mass storage devices 406 may be temporal and/or persistent storage of any type, including, but not limited to, volatile and non-volatile memory, optical, magnetic, and/or solid state mass storage, and so forth. Volatile memory may include, but is not limited to, static and/or dynamic random access memory. Non-volatile memory may include, but is not limited to, electrically erasable programmable read-only memory, phase change memory, resistive memory, and so forth. In some embodiments, one or more of the mass storage devices 406 may be implemented using one or more components of the data storage apparatus 100 and/or the microfluidic droplet storage array 200.

The computer device 400 may further include input/output devices 408 (such as a display (e.g., a touchscreen display), keyboard, cursor control, remote control, gaming controller, image capture device, and so forth) and communication interfaces 410 (such as network interface cards, modems, infrared receivers, radio receivers (e.g., Bluetooth), and so forth). The computer device 400 may include a controller 450 having data storage apparatus control capabilities. In various embodiments, the controller 450 may be configured similarly to the controller 112.

The communication interfaces 410 may include communication chips (not shown) that may be configured to operate the computer device 400 in accordance with a Global System for Mobile Communication (GSM), General Packet Radio Service (GPRS), Universal Mobile Telecommunications System (UMTS), High Speed Packet Access (HSPA), Evolved HSPA (E-HSPA), or Long-Term Evolution (LTE) network. The communication chips may also be configured to operate in accordance with Enhanced Data for GSM Evolution (EDGE), GSM EDGE Radio Access Network (GERAN), Universal Terrestrial Radio Access Network (UTRAN), or Evolved UTRAN (E-UTRAN). The communication chips may be configured to operate in accordance with Code Division Multiple Access (CDMA), Time Division Multiple Access (TDMA), Digital Enhanced Cordless Telecommunications (DECT), Evolution-Data Optimized (EV-DO), derivatives thereof, as well as any other wireless protocols that are designated as 3G, 4G, 5G, and beyond. The communication interfaces 410 may operate in accordance with other wireless protocols in other embodiments.

The above-described computer device 400 elements may be coupled to each other via system bus 412, which may represent one or more buses. In the case of multiple buses, they may be bridged by one or more bus bridges (not shown). Each of these elements may perform its conventional functions known in the art. In particular, system memory 404 and mass storage devices 406 may be employed to store a working copy and a permanent copy of the programming instructions, such as drivers, for the operation of various components of computer device 400, including but not limited to operation of the data storage apparatus 100, including the controller 112 of FIG. 1 (when used as one of mass storage 406), an operating system of computer device 400, controller 450, and/or one or more applications, collectively referred to as computational logic 422. The various elements may be implemented by assembler instructions supported by processor(s) 402 or high-level languages that may be compiled into such instructions.

The permanent copy of the programming instructions may be placed into mass storage devices 406 in the factory or in the field through, for example, a distribution medium (not shown), such as a compact disc (CD), or through communication interface 410 (from a distribution server (not shown)). That is, one or more distribution media having an implementation of the agent program may be employed to distribute the agent and to program various computing devices.

The number, capability, and/or capacity of the elements 408, 410, 412 may vary, depending on whether computer device 400 is used as a stationary computing device, such as a set-top box or desktop computer, or a mobile computing device, such as a tablet computing device, laptop computer, game console, or smartphone. Their constitutions are otherwise known, and accordingly will not be further described.

For some embodiments, at least one of processors 402 may be packaged together with a storage medium having all or portions of computational logic 422 configured to facilitate aspects of embodiments described herein to form a System in Package (SiP) or a System on Chip (SoC).

The computer device 400 may include or otherwise be associated with an appliance state recognition system or apparatus that may include components and/or implement methods described with respect to FIGS. 1-3, such as the data storage apparatus 100, including the controller 112, the method 300, and/or other components or methods in accordance with various embodiments. In some embodiments, one or more components such as processor 402 may be included as a part of the data storage apparatus 100 such as the controller 112.

In various implementations, the computer device 400 may comprise one or more components of a data center, a laptop, a netbook, a notebook, an ultrabook, a smartphone, a tablet, a personal digital assistant (PDA), an ultra mobile PC, a mobile phone, or a digital camera. In further implementations, the computer device 400 may be any other electronic device that processes data.

Figure 5:
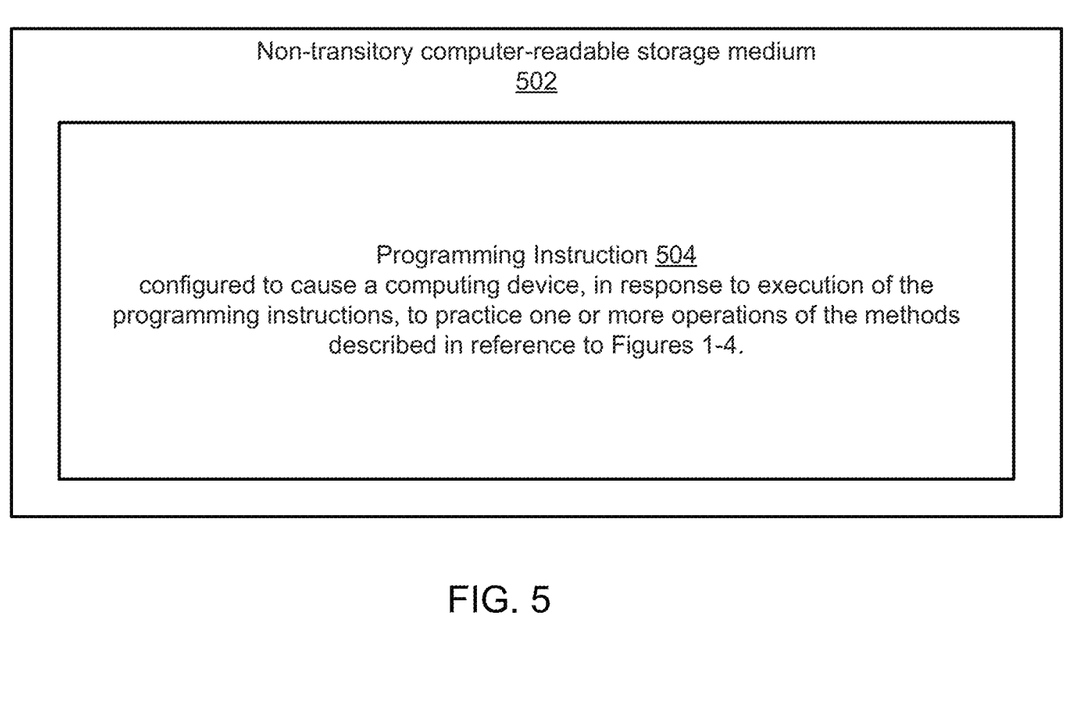
FIG. 5 illustrates an example storage medium with instructions configured to enable an apparatus to practice various aspects of the present disclosure, in accordance with various embodiments.

FIG. 5 illustrates example computer-readable storage medium 502 having instructions configured to practice all or selected ones of the operations associated with the computer device 400, including controller 450, earlier described with respect to FIG. 4; the data storage apparatus 100 including the controller 112 of FIG. 1; and/or the method 300 described with respect to FIG. 3, in accordance with various embodiments. As illustrated, computer-readable storage medium 502 may include a number of programming instructions 504. The storage medium 502 may represent a broad range of non-transitory persistent storage medium known in the art, including but not limited to flash memory, dynamic random access memory, static random access memory, an optical disk, a magnetic disk, etc. Programming instructions 504 may be configured to enable a device, e.g., computer 400, controller 450, and/or controller 112 of FIG. 1, in response to execution of the programming instructions 504, to perform, e.g., but not limited to, various operations described for the controller 112, and/or other components of FIG. 1, or operations shown in process 300 of FIG. 3. In alternate embodiments, programming instructions 504 may be disposed on multiple computer-readable storage media 502. In alternate embodiments, storage medium 502 may be transitory, e.g., signals encoded with programming instructions 504.

Referring back to FIG. 4, for an embodiment, at least one of processors 402 may be packaged together with memory having all or portions of computational logic 422 configured to practice aspects described for the controller 112, and/or other components of FIG. 1, or operations shown in process 300 of FIG. 3. For an embodiment, at least one of processors 402 may be packaged together with memory having all or portions of computational logic 422 configured to practice aspects described for the controller 112, and/or other components of FIG. 1, or operations shown in process 300 of FIG. 3 to form a System in Package (SiP). For an embodiment, at least one of processors 402 may be integrated on the same die with memory having all or portions of computational logic 422 configured to practice aspects described for the controller 112, and/or other components of FIG. 1, or operations shown in process 300 of FIG. 3. For an embodiment, at least one of processors 402 may be packaged together with memory having all or portions of computational logic 422 configured to practice aspects of the controller 112, and/or other components of FIG. 1, operations shown in process 300 of FIG. 3 to form a System on Chip (SoC). For at least one embodiment, the SoC may be utilized in, e.g., but not limited to, a mobile computing device such as a wearable device and/or a smartphone.

Machine-readable media (including non-transitory machine-readable media, such as machine-readable storage media), methods, systems and devices for performing the above-described techniques are illustrative examples of embodiments disclosed herein. Additionally, other devices in the above-described interactions may be configured to perform various disclosed techniques.

Examples

Example 1 may include a data storage apparatus comprising: a microfluidic droplet storage array to store one or more droplets containing one or more information-encoding polymer molecules in one or more droplet storage locations; and an interface coupled with the microfluidic droplet storage array to receive the one or more droplets from a data writer that writes the one or more droplets into the microfluidic droplet storage array.

Example 2 may include the subject matter of Example 1, wherein each of the one or more droplets are to contain at least two information-encoding polymer molecules, wherein the at least two information-encoding polymer molecules are copies of each other to provide redundancy for a reduced error rate.

Example 3 may include the subject matter of any one of Examples 1-2, wherein the one or more information-encoding polymer molecules include deoxyribonucleic acid (DNA).

Example 4 may include the subject matter of Example 3, wherein the DNA is included in the one or more droplets as bare DNA strands.

Example 5 may include the subject matter of any one of Examples 1-4, wherein the interface is a first interface and the apparatus further comprises a second interface coupled with the microfluidic droplet storage array to allow one or more of the one or more information-encoding polymer molecules to move from one or more of the droplet storage locations to a data reader.

Example 6 may include the subject matter of Example 5, further comprising the data reader coupled with the second interface to read stored data based at least in part on the one or more of the one or more information-encoding polymer molecules.

Example 7 may include the subject matter of any one of Examples 1-6, further comprising a controller coupled with the microfluidic droplet storage array, wherein the controller is to generate controlled forces to cause the one or more droplets to move from the interface to one or more locations in the microfluidic droplet storage array.

Example 8 may include the subject matter of Example 7, wherein the interface is a first interface and the controller is also to generate controlled forces to cause one or more of the one or more droplets to move from one or more of the one more locations in the microfluidic droplet storage array to a second interface.

Example 9 may include the subject matter of any one of Examples 7-8, wherein the controlled forces are electrowetting control signals.

Example 10 may include the subject matter of any one of Examples 1-9, wherein the microfluidic droplet storage array has a planar architecture with fluidic droplet transport channels and storage locations in the same plane.

Example 11 may include the subject matter of any one of Examples 1-9, wherein the microfluidic droplet storage array has a layered architecture with fluidic droplet transport channels in a first plane and droplet storage locations in a second plane different than the first plane.

Example 12 may include the subject matter of Example 11, wherein the second plane includes one or more wells and one or more addressable electrodes.

Example 13 may include the subject matter of Example 8, further comprising a data writer coupled with the first interface.

Example 14 may include the subject matter of Example 7, wherein the interface is a first interface and the apparatus further comprises: a data writer coupled with the first interface; a second interface coupled with the microfluidic droplet storage array; and a data reader coupled with the second interface, wherein the data reader includes a nanopore sequencer.

Example 15 may include a method of storing data comprising: receiving a droplet containing one or more information-encoding polymer molecules from a data writer at an interface; and storing the droplet at a storage location in a microfluidic droplet storage array.

Example 16 may include the subject matter of Example 15, further comprising, before receiving the droplet: synthesizing the one or more information-encoding polymer molecules; and encapsulating the one or more information-encoding polymer molecules in the droplet.

Example 17 may include the subject matter of any one of Examples 15-16, wherein the interface is a first interface, the method further comprising: generating a controlled force to move the droplet from the storage location to a second interface.

Example 18 may include the subject matter of any one of Examples 15-17, further comprising: sequencing the one or more information-encoding polymer molecules.

Example 19 may include the subject matter of Example 18, wherein the controlled force is an electrowetting control signal, and wherein sequencing is performed using a nanopore sequencer.

Example 20 may include at least one computer-readable medium comprising instructions stored thereon that, in response to execution of the instructions by one or more processors of a device, cause the device to: generate a controlled force to move a droplet containing one or more information-encoding polymer molecules from an interface with a data writer to a storage location in a microfluidic droplet storage array.

Example 21 may include the subject matter of Example 20, wherein the controlled force is a first controlled force and the instructions are also to cause the device to generate a second controlled force to move the droplet containing the one or more information-encoding polymer molecules from the storage location to a second interface with a data reader.

Example 22 may include the subject matter of any one of Examples 20-21, wherein the instructions are to cause an addressable electrode to eject the droplet from the storage location.

Example 23 may include the subject matter of any one of Examples 20-22, wherein the controlled force includes an electrowetting control signal.

Example 24 may include the subject matter of Example 21, wherein the one or more information-encoding polymer molecules include a first copy of an information-encoding polymer molecule and a second copy of the information-encoding polymer molecule, and the instructions are also to cause the device to: move a first portion of the droplet, including the first copy of the information-encoding polymer molecule, to the data reader; and move a second portion of the droplet, including the second copy of the information-encoding polymer molecule, to an amplification module.

Example 25 may include the subject matter of Example 24, wherein the droplet is a first droplet and the instructions are also to cause the device to: generate one or more copies of the second copy of the information-encoding polymer molecule; encapsulate the one or more copies of the second copy of the information-encoding polymer molecule in a second droplet; and store the second droplet in the microfluidic droplet storage array.

Example 26 may include the subject matter of any one of Examples 20-22, wherein the controlled force includes one or more of an acoustic force, a dielectrophoretic force, or an electrophoretic force.

Example 27 may include the subject matter of any one of Examples 1-9, wherein the microfluidic droplet storage array includes a plurality of transport layers and a plurality of storage layers interconnected by vias that can transport one or more of fluids, droplets, or beads.

Example 28 may include a include a data storage apparatus comprising: a microfluidic storage array to store one or more information-encoding polymer molecules attached to one or more beads in one or more bead storage locations; and an interface coupled with the microfluidic storage array to receive the one or more beads from a data writer that writes the one or more beads with one or more attached information-encoding polymers into the microfluidic droplet storage array.

Example 29 may include the subject matter of Example 28, wherein the one or more attached information-encoding polymer molecules are deoxyribonucleic acid (DNA) molecules.

Various embodiments may include any suitable combination of the above-described embodiments including alternative (or) embodiments of embodiments that are described in conjunctive form (and) above (e.g., the "and" may be "and/or"). Furthermore, so me embodiments may include one or more articles of manufacture (e.g., non-transitory computer-readable media) having instructions, stored thereon, that when executed result in actions of any of the above-described embodiments. Moreover, some embodiments may include apparatuses or systems having any suitable means for carrying out the various operations of the above-described embodiments.

Although certain embodiments have been illustrated and described herein for purposes of description, a wide variety of alternate and/or equivalent embodiments or implementations calculated to achieve the same purposes may be substituted for the embodiments shown and described without departing from the scope of the present disclosure. This application is intended to cover any adaptations or variations of the embodiments discussed herein. Therefore, it is manifestly intended that embodiments described herein be limited only by the claims.

Where the disclosure recites "a" or "a first" element or the equivalent thereof, such disclosure includes one or more such elements, neither requiring nor excluding two or more such elements. Further, ordinal indicators (e.g., first, second or third) for identified elements are used to distinguish between the elements, and do not indicate or imply a required or limited number of such elements, nor do they indicate a particular position or order of such elements unless otherwise specifically stated.

What is claimed is:

1. A data storage apparatus comprising:
   a microfluidic droplet storage array having a plurality of droplet storage locations;
   a first interface coupled with the microfluidic droplet storage array, and having a data writer, to receive input data, synthesize one or more information-encoding polymer molecules based at least in part on the input data, attach the one or more information-encoding polymer molecules to one or more particles or beads, and encapsulate the one or more particles or beads into one or more droplets to be stored into the microfluidic droplet storage array;
   a controller coupled with the first interface and the microfluidic droplet storage array to generate a first controlled force to cause the one or more droplets to move from the first interface to one or more of the plurality of droplet storage locations to store the one or more droplets in the microfluidic droplet storage array; and
   a second interface coupled with the microfluidic droplet storage array and the controller, and having a data reader, to retrieve the one or more droplets from the microfluidic droplet storage array, wherein the controller is further arranged to generate a second controlled force to cause the one or more droplets to move from the one or more of the plurality of droplet storage locations of the microfluidic droplet storage array to the second interface.

2. The data storage apparatus of claim 1, wherein at least two information-encoding polymer molecules of the one or more droplets are copies of each other to provide redundancy for a reduced error rate.

3. The data storage apparatus of claim 1, wherein the information-encoding polymer molecules of the one or more droplets include deoxyribonucleic acid (DNA).

4. The data storage apparatus of claim 3, wherein the DNA is included as bare DNA strands.

5. The data storage apparatus of claim 1, wherein to generate the first and second controlled forces, the controller generates first and second electrowetting control signals.

6. The data storage apparatus of claim 1, wherein the microfluidic droplet storage array has a planar architecture with fluidic droplet transport channels and storage locations in a same plane.

7. The data storage apparatus of claim 1, wherein the microfluidic droplet storage array has a layered architecture with fluidic droplet transport channels in a first plane and droplet storage locations in a second plane underneath the first plane.

8. The data storage apparatus of claim 7, wherein the second plane includes one or more wells and one or more addressable electrodes.

9. A method of storing data comprising:
   receiving input data, at a data writer of a microfluidic droplet storage device;
   synthesizing, by the data writer, one or more information-encoding polymer molecules based at least in part on the input data;
   attaching, by the data writer, the one or more information-encoding polymer molecules to one or more particles or beads;
   encapsulating, by the data writer, the one or more particles or beads into one or more droplets;
   generating, by a controller of the microfluidic droplet storage device, coupled with the data writer, a first controlled force to move the one or more droplets from the data writer to one or more droplet storage locations of the microfluidic droplet storage device to store the one or more droplets in the microfluidic droplet storage device; and
   generating, subsequently, by the controller, a second controlled force to move the one or more droplets from the one or more droplet storage locations to a data reader of the microfluidic droplet storage device, coupled with the controller.

10. The method of claim 9, wherein synthesizing, by the data writer, one or more information-encoding polymer molecules comprises sequencing, by the data writer, the one or more information-encoding polymer molecules.

11. The method of claim 10, wherein generating, by the controller, the second controlled force comprises generating, by the controller, an electrowetting control signal, and wherein sequencing, by the data writer, comprises using a nanopore sequencer.

12. At least one non-transitory computer-readable medium comprising instructions stored thereon that, in response to execution of the instructions by one or more processors of a microfluidic droplet storage device, cause the device to:
   receive input data, at a data writer of the microfluidic droplet storage device;
   synthesize, with the data writer, one or more information-encoding polymer molecules based at least in part on the input data;
   attach, with the data writer, the one or more information-encoding polymer molecules to one or more particles or beads;
   encapsulate, with the data writer, the one or more particles or beads into one or more droplets;
   generate, with a controller of the microfluidic droplet storage device, a first controlled force to move the one or more droplets from the data writer to one or more droplet storage locations in the microfluidic droplet storage device; and
   generate, with the controller, a second controlled force to move the one or more droplets from the one or more droplet storage locations to a data reader of the microfluidic droplet storage device.

13. The at least one non-transitory computer-readable medium of claim 12, wherein to generate the second controller force comprises to cause an addressable electrode of the microfluidic droplet storage device to eject the one or more droplets from the one or more droplet storage locations.

14. The at least one non-transitory computer-readable medium of claim 12, wherein to generate the first or second controlled force includes to generate an electrowetting control signal.

15. The at least one non-transitory computer-readable medium of claim 12, wherein the one or more information-encoding polymer molecules include a first copy of a first information-encoding polymer molecule and a second copy of the first information-encoding polymer molecule, and wherein to generate, with the controller, a second controlled force to move the one or more droplets to a data reader of the microfluidic droplet storage device includes to:
   generate, with the controller, the second controlled force to move the first copy of the information-encoding polymer molecule to the data reader; and move the second copy of the information-encoding polymer molecule to an amplification module of the microfluidic droplet storage device.

* * * * *